United States Patent

Khuri et al.

[11] Patent Number: 5,957,944
[45] Date of Patent: Sep. 28, 1999

[54] METHOD FOR TREATMENT OF TRIGGER FINGER

[75] Inventors: Suheil M. Khuri, Albany; Richard R. Whipple, Glenmont, both of N.Y.

[73] Assignee: Biomet, Inc., Warsaw, Ind.

[21] Appl. No.: 09/033,025

[22] Filed: Mar. 2, 1998

Related U.S. Application Data

[62] Division of application No. 08/556,733, Nov. 7, 1995, abandoned.

[51] Int. Cl.⁶ .................................................. A61B 17/32
[52] U.S. Cl. ............................................ 606/170; 128/898
[58] Field of Search ................................. 606/167, 170; 128/898

[56] References Cited

U.S. PATENT DOCUMENTS

| | | | |
|---|---|---|---|
| 2,649,860 | 8/1953 | Royer | 128/314 |
| 2,764,814 | 10/1956 | Jecker et al. | 30/294 |
| 2,838,049 | 6/1958 | Eisenhofer et al. | 128/305 |
| 3,844,272 | 10/1974 | Banko | 128/2 B |
| 4,497,320 | 2/1985 | Nicholson et al. | 128/305 |
| 5,085,663 | 2/1992 | Tarr | 606/172 |
| 5,122,152 | 6/1992 | Mull | 606/170 |
| 5,176,695 | 1/1993 | Dulebohn | 606/170 |
| 5,217,476 | 6/1993 | Wishinsky | 606/167 |
| 5,217,477 | 6/1993 | Lager | 606/167 |
| 5,282,816 | 2/1994 | Miller et al. | 606/167 |
| 5,292,330 | 3/1994 | Shutt | 606/170 |
| 5,297,340 | 3/1994 | Kahlcke | 30/155 |
| 5,304,190 | 4/1994 | Reckelhoff et al. | 606/170 |
| 5,323,765 | 6/1994 | Brown | 128/4 |
| 5,341,822 | 8/1994 | Farr et al. | 128/898 |
| 5,353,812 | 10/1994 | Chow | 128/898 |
| 5,387,222 | 2/1995 | Strickland | 606/167 |
| 5,397,333 | 3/1995 | Knoepfler | 606/170 |
| 5,413,580 | 5/1995 | Stephenson | 606/170 |
| 5,458,611 | 10/1995 | Resnick et al. | 606/167 |
| 5,480,408 | 1/1996 | Chow | 606/167 |
| 5,531,232 | 7/1996 | Hill | 128/898 |
| 5,782,850 | 7/1998 | Ro | 606/167 |

FOREIGN PATENT DOCUMENTS

| | | | |
|---|---|---|---|
| 3416490 | 2/1986 | Germany | 606/167 |
| 1389766 | 4/1988 | U.S.S.R. | 606/167 |

*Primary Examiner*—Jeffrey A. Smith
*Attorney, Agent, or Firm*—Harness, Dickey & Pierce, P.L.C.

[57] ABSTRACT

Trigger finger release surgery is performed percutaneously using an instrument, having a prong with a blade about 3 to 7 mm from the distal end of said prong. The prong is inserted into the flexor tendon such that the blade is positioned adjacent the flexor sheath. Flexion or extension of the afflicted finger moves the flexor tendon along with the inserted instrument along the length of the sheath causing the blade to cut the sheath and release the tendon. The movement of the tendon safely directs the knife through the pulley sheath.

20 Claims, 2 Drawing Sheets

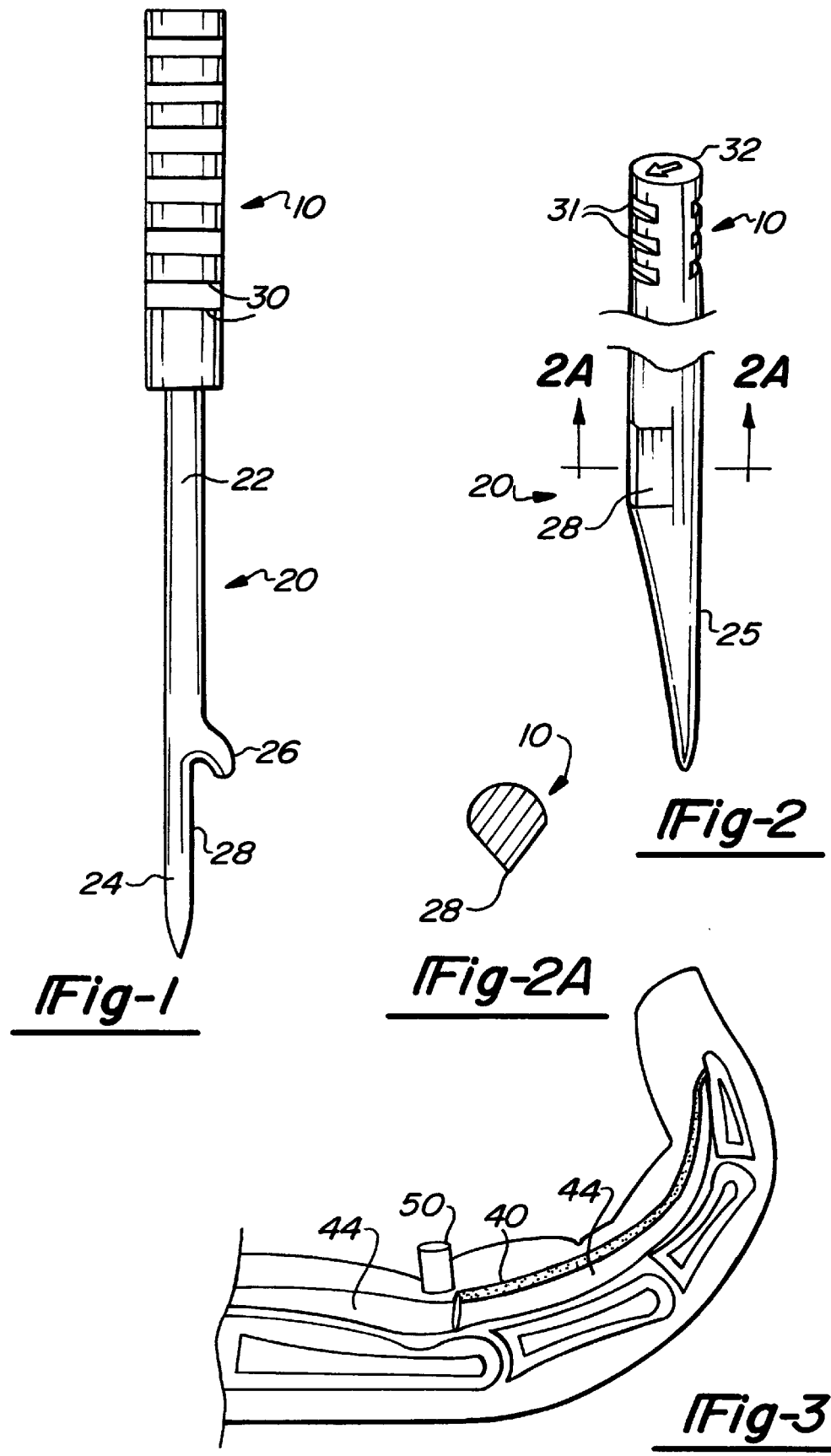

METHOD FOR TREATMENT OF TRIGGER FINGER

This application is a division of application Ser. No. 08/556,733, now abandoned, filed on Nov. 7, 1995.

TECHNICAL FIELD

The invention relates to surgical instruments and more particularly to a surgical instrument for performing a trigger finger release operation. In addition, the invention also relates to a method of using such a surgical instrument in performing a trigger finger release operation.

BACKGROUND OF THE INVENTION

Trigger finger, as the term is commonly used, refers to an abnormal condition in which flexion or extension of a finger may be momentarily obstructed, causing spasms and a snapping of the finger. In severe circumstances this condition may lock a finger in a single position or possibly effect several fingers of a person's hand. Trigger finger is most commonly experienced among middle-aged persons and, as the name implies, typically afflicts the middle finger or ring finger. This condition is commonly caused by an obstruction which prevents the flexor tendon from moving freely within the protective sheath. Such an obstruction may be caused by the formation of a nodule on the flexor tendon or by the swelling of the flexor tendon itself; the nodule or swelling of the tendon restricts the movement of the tendon within the sheath thereby causing the spastic or uncontrolled movement.

Today this problem is typically treated using conventional surgical techniques and instruments in an open operative procedure. An incision is made in the palm of the hand adjacent the distal crease in the palm. The flexor sheath is then explored through the incision and a cutting instrument is inserted through the incision in order to cut a portion of the sheath. Cutting a portion of the sheath over the flexor tendon relieves the constriction, "releasing" the tendon, and eliminating the spastic movement. However, when cutting the sheath it is important not to disturb or cut the neurovascular bundles located near the tendon. The incisions are subsequently sewn shut and allowed to heal. However, even after the hand has fully healed from such an operative procedure the person is typically left with an unsightly scar. In addition, the use of such conventional techniques often requires that the procedure be performed in an operating room and adherence to strict protocols which result in the expenditure of considerable time and money.

Therefore, there exists a need for a percutaneous method of treating trigger finger which does not require significant open incisions. Moreover, there is a need for a percutaneous method of treating trigger finger which allows the procedure to be performed as an office procedure. There likewise exists a need for a method and apparatus which allow medical professionals to quickly and safely perform such a procedure without risk to the numerous neurovascular bundles located throughout the hand.

SUMMARY OF THE INVENTION

The aforesaid needs are met and the problems of the prior art overcome by the present invention which in one aspect includes a surgical tool having an instrument head with a prong and a blade edge, the blade edge running substantially parallel to the longitudinal axis of the instrument head, and the prong extending a distance less than the combined width of a pulley sheath and flexor tendon beyond the end of said blade edge and terminating in a point.

A further aspect of the invention includes a surgical tool comprising an instrument head extending from a handle, the instrument head having a first prong and a second prong extending therefrom. The first prong extends beyond the distal end of the second prong a distance less than the combined width of a pulley sheath and flexor tendon. The first prong also has a blade edge along a portion of its length. The blade edge may extend from the proximal end of the first prong toward the distal end along less than about half of the length of the first prong.

A further aspect of the invention includes a method of cutting a flexor sheath, comprising: (1) locating a flexor tendon and sheath; (2) inserting a surgical tool, having a blade edge and a prong, into the flexor tendon such that the prong extends into the flexor tendon and the blade edge is positioned adjacent the sheath; (3) moving the flexor tendon relative to the sheath wherein the blade edge cuts the sheath; and then (4) removing the tool. Moving the flexor tendon may comprise extending or flexing the finger.

DESCRIPTION OF THE DRAWINGS

FIG. 1 is a side view of a surgical instrument of the present invention.

FIG. 2 is a partially elevated side view of a single pronged surgical instrument of the present invention.

FIG. 2a is a front view of the blade edge from FIG. 2.

FIG. 3 is a cross-sectional side view of a finger having a cannula inserted therein.

DESCRIPTION OF A PREFERRED EMBODIMENT

Figure 4:
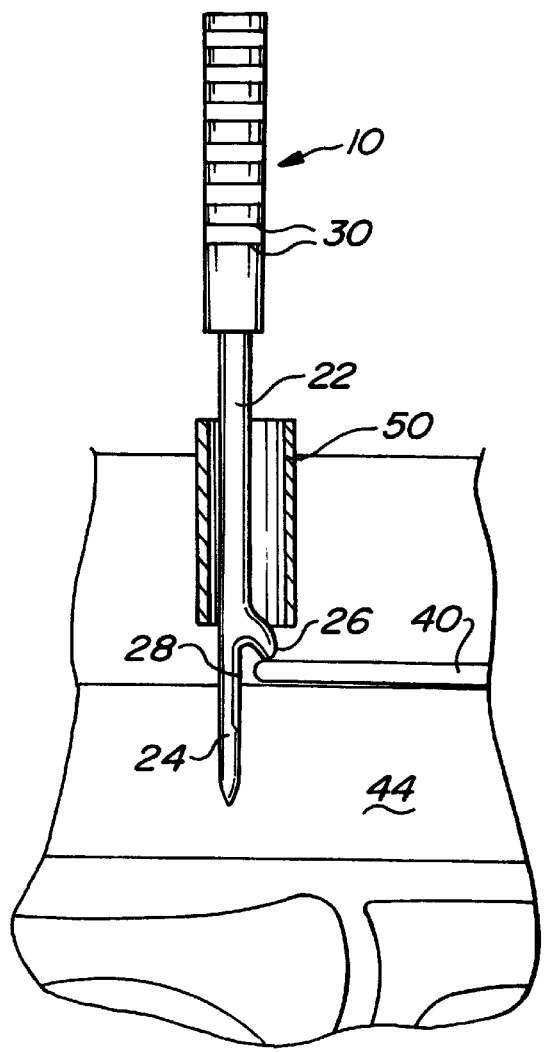
FIG. 4 is a cross-sectional side view of the instrument of FIG. 1 inserted within the cannula of FIG. 3.

A surgical cutting instrument which may be used to effect a percutaneous trigger finger release operation may be seen in reference to FIGS. 1 and 2. In reference to FIG. 1, one embodiment may comprise a surgical instrument having a handle 10 and an instrument head 20; the instrument head 20 in turn, having a shaft 22, the distal portion of which may form two separate extensions or prongs 24 and 26. The first-prong 24 may extend approximately 3 to 10 mm, more preferably, 3 to 7 mm. The distal portion of the first prong may form a point which is preferably defined such that it readily penetrates tissue, such as the skin or a tendon. The portion of the first prong proximate the second prong may have a blade edge 28 running parallel to the longitudinal axis of the shaft 22. The length of the first prong extending beyond the distal end of the second prong should be less than the combined width of the pulley sheath 40 and flexor tendon 44 (see FIG. 4). Preferably the first prong 24 extends about 2 to 5 mm beyond the distal end of the second prong 26. The blade edge 28 on the first prong 24 may extend toward the distal end, preferably along less than about half its length. The blade edge 28 may also continue up the first prong 24 curving around the end of the shaft 22 and along the length of the second prong 26, forming a "hook" shaped blade edge as shown in FIG. 1. The second prong 26 may extend from the shaft 22 a distance less than the blade edge 28 along the first prong 24 with the distal end being blunt. However, with regard to the lengths of the first and second prongs, one skilled in the art will appreciate that size of patients' tendons and sheaths vary and, therefore, the exact measurement of the instrument will likewise vary.

The handle 10 of the instrument, connected to or extending from the shaft, may have grooves 30, as shown in FIG. 1, or be coated with non-slip materials in order to facilitate handling by the medical professional. As shown in FIG. 2, the grooves 31 may also be positioned in line with the blade edge to allow the instrument to be rotated with another device. As used herein "in line" means positioned only on the same side and the opposed side relative to the blade edge. In addition, the terminal end of the handle 10 may have markings thereon which indicate the direction the blade edge is facing, such as an arrow 32 or other marking.

An alternative embodiment may be seen in FIGS. 2 and 2a. The instrument head 20 has a blade edge 28 running parallel to the longitudinal axis of the tool, such that when the instrument is inserted within the hand, as described herein below, the blade edge 28 will be perpendicular to the sheath. Preferably the blade is recessed within the instrument head 20 and semi-circular in shape. The blade edge 28 is positioned on the instrument such that when the prong 25 is inserted into the tendon the blade edge 28 is adjacent the sheath. Generally the blade edge will be about 2 to 4 mm in length, the center of which may be positioned 3 to 8 mm from the distal end of the prong 25. Opposite the handle 10 and adjacent the recessed blade edge 28, prong 25 extends away from the handle 10. The prong 25 may gradually tapper into a point at its distal end, in a preferred embodiment the largest diameter of the prong is proximate to the recessed blade edge 28. Preferably the point is sharp enough to allow it to be readily inserted into tissue, such as skin or a tendon.

The instrument head and the handle may be made out of stainless steel, although other materials commonly used for surgical instruments, such as titanium and super alloys, may also be used. Such materials should be capable of withstanding common sterilization procedures as well as being sufficiently durable so as not to bend or fail during the release procedure.

The percutaneous method of releasing a trigger finger of the present invention generally comprises (1) locating the restriction upon the flexor tendon of the afflicted finger, (2) inserting a surgical instrument, having a prong and a blade, into the tendon, (3) flexing or extending the afflicted finger with the instrument in place and (4) removing the surgical instrument.

In order to treat the condition, it is first necessary to identify the afflicted finger and the corresponding constriction of the tendon. The path of the flexor tendons are generally well known to one skilled in the art and may also be more precisely located by manually feeling the hand. Typically, the constriction occurs where the sheath ends, which is where the flexor tendon crosses the distal crease in the palm of the hand. Accordingly, the instrument may often be inserted proximate to the end of the flexor sheath. However, the instrument may also be inserted into the tendon at an area covered by the sheath. The exact location of insertion may be determined by the attending medical professional. The point of insertion may then be marked by means well known in the art.

Prior to insertion of the surgical instrument the hand should be thoroughly cleaned and sterilized. In addition, the area to be operated upon should be fully anesthetized. However, since this is a percutaneous procedure the present method requires only a local anesthetic and is capable of being performed in a doctor's office rather than on an out-patient basis. One skilled in the art will understand that the application of the local anesthetic will vary with the particular patient, each application and dosage varying with factors well known to a skilled medical professional.

A skin knife may be initially used to cut the skin in the desired location, typically adjacent to the proximal end of the flexor pulley 40. An example of preferred skin knives include a Beaver, No. 11 blade or No. 15 blade. A cannula 50 may then inserted into the opening made by the knife, as shown in FIG. 3. A blunt obturator may then be inserted into the cannula, allowing manipulation of the obturator (not shown) and cannula to more precisely locate the top center of the tendon 44, relative to the sides thereof, and to identify the proximal end of the flexor sheath 40. However, insertion of the cannula and obturator is not believed to be necessary, although it is preferred as it will aid in the accurate location of the top of the flexor tendon and sheath, and also acts to prevent damage to the neurovascular bundles when inserting the surgical instrument.

Once the top of the flexor tendon 44 has been located the obturator may be removed from the cannula. While maintaining the cannula 50 in place, a surgical instrument, such as one shown in FIGS. 1 and 2, may be inserted into the tendon through the cannula. Although preferred surgical instruments are shown in FIGS. 1 and 2, use of other surgical instruments in the present process may be possible. Suitable surgical instruments should have an instrument head having an extension capable of being inserted into the tendon with a blade edge located about 3 to 10 mm from the distal end of the extension. As shown in FIG. 4, the extension, prong 24, is inserted into the tendon 44 such that the blade 28 is positioned at a depth in the hand equal to that of the sheath 40 and such that the blade edge is facing the sheath 40.

When using the instrument of FIG. 1, the first prong 24 is inserted into the tendon until the blunt end of the second prong 26, which acts as a stopping mechanism, rests upon either the flexor tendon 44 or sheath 40. This acts to insure proper positioning of the blade edge 28 relative to the sheath 40 as discussed above. However, when using the device of FIG. 2, or an alternate instrument without a self-aligning feature, the blade edge 28 may be aligned by inserting the instrument a preset distance or alternatively inserting the prong to the surface of the bone, which acts to stop the instrument, and then retracting the instrument a set distance to insure alignment of the blade with the sheath.

Figure 5:
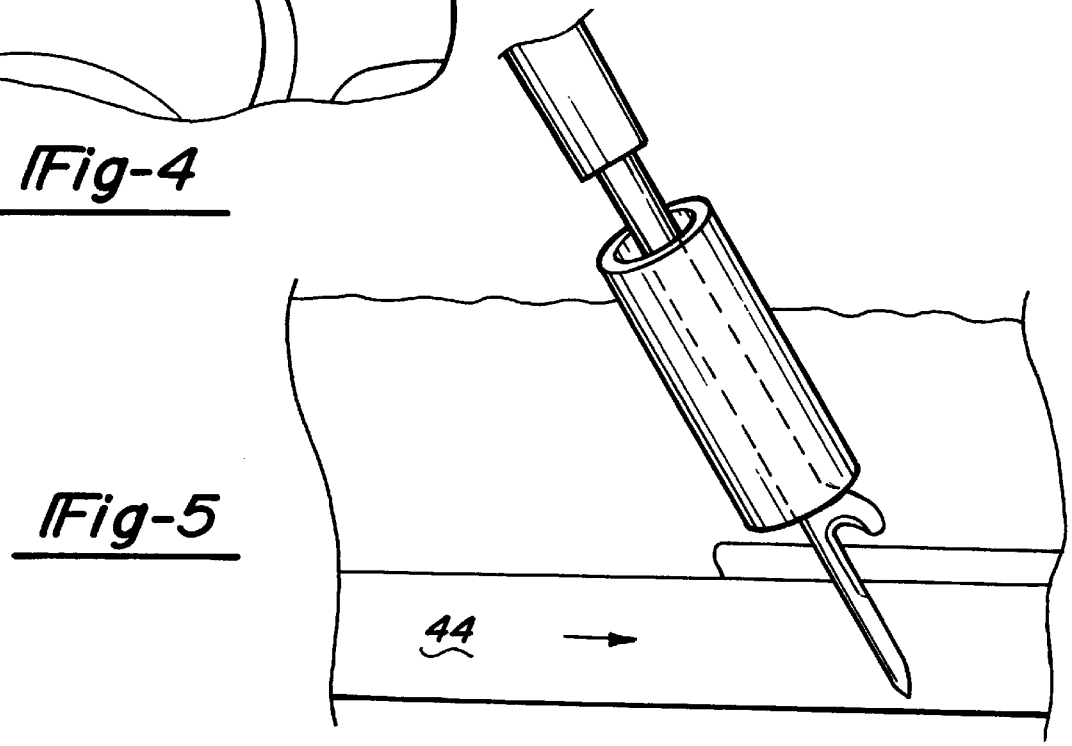
FIG. 5 is a cross-sectional side view of FIG. 4 after extension of the finger.

After the surgical instrument has been placed within the flexor tendon 44 of the afflicted finger, the finger is flexed or extended thereby causing the tendon 44 to move in relation to the sheath 40. This movement of the flexor tendon 44 also acts to move the surgical instrument and its blade edge 28 along the plain of the sheath such that the blade edge 28 cuts the sheath 40 relieving the constriction. In reference to FIG. 5, passive extension of the finger advances the tendon distally thereby moving the blade edge 28 through the flexor sheath 40. The prong serves to guide the knife in the proper direction during tendon motion. Active flexion of the finger can be done with the blade cutting edge reversed, this cuts the sheath from distal to proximal as the flexor tendon with the blade and cannula, are pulled proximally by the patient. The flexion or extension of the afflicted finger may be performed several times to insure the cutting of the sheath. The afflicted finger may then be returned to its original position and the cutting instrument removed from the hand through the cannula, followed by removal of the cannula.

After removal of the cutting instrument and the cannula the minor incision may be closed. Typically the incision would only be 2 to 5 mm and therefore, in many instances stitches should not be required. Often a steri-strip or other non-surgical bandage may be used to cover the wound, allowing the wound to heal substantially unaided.

If the instrument is inserted in the flexor tendon immediately adjacent the sheath, the instrument should be inserted with the afflicted finger flexed, allowing extension of the finger to advance the blade through the sheath. In an alternate embodiment, the cutting instrument may be inserted into the flexor tendon in an area covered by the sheath, as opposed to the area immediately adjacent to the end of the sheath as shown in FIG. 4. In this instance, the insertion of the instrument may be done with the finger placed in a partially flexed position. After inserting the cutting instrument into the tendon, such that the blade is at the appropriate depth, the afflicted finger may be fully extended. As above, the movement of the tendon pulls the cutting instrument along the plain of the sheath thereby cutting the same. Thereafter, the cutting instrument may be rotated 180° such that the blade faces opposite the direction originally inserted. The afflicted finger may be then be flexed, past the finger's original partially flexed position, to a fully flexed position. This action pulls the cutting instrument beyond its original position increasing the length of sheath cut. The flexion and extension of the afflicted finger, and a respective rotation of the blade edge, may be performed several times to insure cutting of the sheath. Thereafter the cutting instrument and cannula may be removed and the opening appropriately treated.

This technique is advantageous in that the tendon directs the knife through the obstructing pulley sheath. This forces a safe division of the sheath without damaging surrounding soft tissues, it is done in a percutaneous fashion without a formal open incision.

While the present invention has been particularly shown and described with reference to preferred embodiments thereof, it will be understood to those skilled in the art that various changes in form and details may be made therein without departing from the scope of the invention.

What is claimed:

1. A method of cutting a flexor sheath, comprising:
   locating a flexor tendon and sheath;
   inserting a surgical tool, said surgical tool having a blade edge and a prong, into a flexor tendon wherein the prong extends into the flexor tendon and the blade edge is positioned adjacent said sheath;
   moving said flexor tendon relative to said sheath wherein said blade edge cuts said sheath; and
   removing said tool.

2. The method of claim 1 wherein said tendon is the flexor tendon of a finger.

3. The method of claim 2 wherein moving said flexor tendon comprises extending said finger.

4. The method of claim 3 wherein said tool is inserted with the finger partially flexed and said tendon is moved by extending said digit.

5. The method of claim 2 wherein moving said flexor tendon comprises flexing said finger.

6. The method of claim 2 wherein said tool is inserted with the finger partially flexed; and after moving said flexor tendon relative to said sheath the blade edge is rotated 180°, then the flexor tendon is moved in the opposite direction.

7. The method of claim 1 further comprising inserting a cannula over said flexor tendon prior to inserting said instrument and removing said cannula after removing said instrument.

8. The method of claim 7 further comprising inserting an obturator through said cannula and manipulating the obturator to locate the top of said flexor tendon prior to inserting said instrument.

9. A method for cutting a flexor sheath with a surgical tool having a first prong and a blade edge adjacent to the first prong, said method comprising the steps of:
   locating a flexor tendon and a sheath;
   inserting the first prong of the surgical tool into the flexor tendon up to a depth where the blade edge is operable to cut the sheath;
   moving the flexor tendon relative to the sheath, whereby the first prong moves relative to the sheath with the blade edge cutting the sheath; and
   removing the surgical tool.

10. The method as defined in claim 9 wherein the step of inserting the first prong further includes the step of inserting the first prong of the surgical tool into the flexor tendon substantially adjacent to the sheath with the blade edge facing and being adjacent to the sheath whereby the blade edge is directed into the sheath as the flexor tendon is moved.

11. The method as defined in claim 9 wherein the step of inserting the first prong further includes the step of inserting the first prong of the surgical tool into both the flexor tendon and the sheath up to a depth where the blade edge is operable to cut the sheath as the flexor tendon is moved.

12. The method as defined in claim 9 wherein the surgical tool further includes a second prong located proximally from the first prong, and wherein the step of inserting the first prong further includes the step of inserting the first prong of the surgical tool into the flexor tendon up to a depth where the second prong engages the sheath.

13. The method as defined in claim 9 wherein the flexor tendon is a flexor tendon of a finger and wherein the step of moving the flexor tendon includes extending and flexing the finger.

14. The method as defined in claim 13 further comprising the steps of:
   flexing the finger;
   inserting the first prong of the surgical tool into the flexor tendon of the flexed finger; and
   extending the flexed finger to advance the blade edge through the sheath.

15. The method as defined in claim 13 further comprising the steps of:
   extending the finger;
   inserting the first prong of the surgical tool into the flexor tendon of the extended finger; and
   flexing the extended finger to advance the blade edge through the sheath.

16. A method for cutting a flexor sheath of a finger, said method comprising the steps of:
   providing a surgical tool having a first prong and a blade edge adjacent to the first prong;
   locating a flexor tendon and a sheath of the finger;
   inserting the first prong of the surgical tool into the flexor tendon of the finger;
   moving the finger, whereby the flexor tendon moves relative to the sheath and the blade edge cuts the sheath; and
   removing the surgical tool.

17. The method as defined in claim 16 wherein the steps of inserting the first prong further includes the step of engaging both the flexor tendon and the sheath.

18. The method as defined in claim 16 further comprising the steps of:

moving the finger in a first direction to cause the blade edge to cut the sheath along the first direction;

turning the blade edge to a second direction; and moving the finger in the second direction to cause the blade edge to cut the sheath along the second direction.

19. The method as defined in claim 16 wherein the step of providing the surgical tool further includes the step of providing a second prong located proximally from the first prong and wherein the step of inserting the first prong further includes the step of inserting the first prong of the surgical tool into the flexor tendon of the finger up to a depth where the second prong engages the sheath.

20. The method as defined in claim 16 further comprising the steps of:

inserting a cannula relative to the flexor tendon and the sheath; and inserting the first prong of the surgical tool through the cannula and into the flexor tendon.

\* \* \* \* \*

UNITED STATES PATENT AND TRADEMARK OFFICE
CERTIFICATE OF CORRECTION

PATENT NO.   : 5,957,944
DATED        : September 28, 1999
INVENTOR(S)  : Suheil M. Khuri, Richard R. Whipple It is certified that error appears in the above-identified patent and that said Letters Patent is hereby corrected as shown below:

Column 2,
Line 47, "first-prong" should be -- first prong --

Column 3,
Line 28, delete "tapper" and substitute -- taper -- therefor

Column 4,
Line 9, after "then" insert -- be --

Column 5,
Line 18, delete "plain" and substitute -- plane -- therefor
Line 21, delete 1st occurrence of "be"

Signed and Sealed this

Twenty-sixth Day of February, 2002

Attest:

JAMES E. ROGAN
Attesting Officer    Director of the United States Patent and Trademark Office